United States Patent [19]

Shim

[11] 3,936,514

[45] *Feb. 3, 1976

[54] POLYALKYLENE GLYCOL VINYL PHOSPHATES

[75] Inventor: Kyung S. Shim, Irvington, N.Y.

[73] Assignee: Stauffer Chemical Company, Westport, Conn.

[*] Notice: The portion of the term of this patent subsequent to June 25, 1991, has been disclaimed.

[22] Filed: Sept. 6, 1974

[21] Appl. No.: 502,992

Related U.S. Application Data

[63] Continuation-in-part of Ser. No. 410,674, Nov. 12, 1973, which is a continuation-in-part of Ser. No. 86,313, Nov. 2, 1970, Pat. No. 3,819,750, which is a continuation-in-part of Ser. No. 63,262, Aug. 6, 1970, abandoned.

[52] U.S. Cl. ........ 260/929; 260/2.5 A; 260/2.5 BB; 260/18 TN
[51] Int. Cl.² .......................................... C07F 9/02
[58] Field of Search ................................... 260/929

[56] References Cited
UNITED STATES PATENTS 3,819,750   6/1974   Shim .................. 260/929

Primary Examiner—Anton H. Sutto

[57] ABSTRACT

Polyalkylene glycol vinylphosphates having the formula:

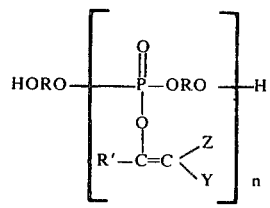

are provided wherein R is a polyalkylene glycol residue, $n$ is an integer from 1 to about 100, R' is selected from the group consisting of hydrogen, alkyl and haloalkyl and Z and Y are each selected from the group consisting of halogen, hydrogen and alkyl, provided Z and Y are not both hydrogen or alkyl. Also provided are flame retardant polymeric compositions containing said phosphates alone or in combination with other reactive or non-reactive flame retardants.

8 Claims, No Drawings

POLYALKYLENE GLYCOL VINYL PHOSPHATES

RELATED APPLICATION

This application is a continuation-in-part of U.S. application Ser. No. 410,674, filed Nov. 12, 1973, which is a continuation-in-part of U.S. application Ser. No. 86,313 filed Nov. 2, 1970, now U.S. Pat. No. 3,819,750, which, in turn, is a continuation-in-part of Application Ser. No. 63,262, filed Aug. 6, 1970, now abandoned.

SUMMARY OF THE INVENTION

This invention relates to polyalkylene glycol vinyl phosphonates and to flame retardant polymeric compositions containing said phosphates alone or in combination with other flame retardants.

BACKGROUND OF THE INVENTION

In the polyurethane field, increased interest is being shown in compounds which can be added to the polyurethane polymers to act as fire retardant agents. Particular interest is being shown in compounds which have functional groups reactive with the polyol or polyisocyanate used in preparing the polyurethane so that the fire retardant agent can be copolymerized into the polymer chain. One such group of compounds of this type are the polyalkylene glycol polyphosphites and phosphonates. In general, these materials are prepared by transesterifying a secondary phosphite with a polyalkylene glycol in the presence of an alkaline catalyst such as sodium phenolate or sodium methylate. However, many of these materials have relatively high acidity causing them to react with and thereby deactivate certain catalyst systems generally used in the formation of polyurethane polymers such, for example, as tertiary amine compounds. To alleviate this problem, the polyalkylene glycol phosphonates have heretofore been reacted with materials such as alkylene oxides in order to reduce the number of acid groups on the phosphorus. However, addition of the alkylene groups onto the phosphorus has decreased the relative flame retardancy of these compounds. Alternatively, secondary polyalkylene glycol phosphites have been reacted with carbon tetrachloride or chloral in order to add flame retardant chlorine atoms to the molecule. However, the phosphonates formed in this manner are still relatively high in acidity.

Therefore, it is an object of the present invention to produce a class of compounds which are compatible with polyurethane foams, which can be copolymerized therewith, which have a high degree of flame retardancy and which are relatively low in acidity. Various other objects and advantages of this invention will be apparent from a reading of the disclosure which follows hereinafter.

TECHNICAL DESCRIPTION OF THE INVENTION

It has now been discovered that this object can be realized by employing novel polyalkylene glycol vinyl phosphates, produced by transesterifying a tertiary phosphite with a polyalkylene glycol, and reacting the polyphosphite so obtained with a carbonyl compound. The novel compounds of the present invention have a formula corresponding to:

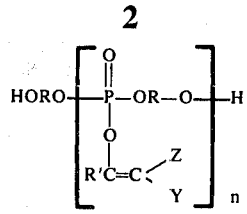

wherein $n$ is a number having a value of from 1 to about 100, Y and Z are each selected from the group consisting of hydrogen halogen or alkyl, having from 1 to about 4 carbon atoms, R is a polyalkylene glycol residue and R' is hydrogen, alkyl or haloalkyl haivng from 1 to 4 carbon atoms, provided Z and Y are not both hydrogen or alkyl.

The term "polyalkylene glycol residue" is meant to designate that portion remaining after two hydroxyl groups have been removed from a polyalkylene glycol having the formula:

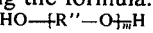

wherein $R''$ is an alkylene group of from 2 to about 20 carbon atoms, and $m$ designates the number of repeating alkylene ether units and is normally from 2 to about 20.

Illustrative of the compounds of the present invention are the following:

tripropylene glycol-β, β-dichlorovinyl phosphate
bis(tripropylene glycol-β, β-dichlorovinyl phosphate)
tris(tripropylene glycol-β, β-dichlorovinyl phosphate)
poly(tripropylene glycol-β,β-dichlorovinyl phosphate)
dipropylene glycol-β, β-dichlorovinyl phosphate
bis(dipropylene glycol-β, β-dichlorovinyl phosphate)
tris(dipropylene glycol-β, β-dichlorovinyl phosphate)
poly(dipropylene glycol-β, β-dichlorovinyl phosphate)
triethylene glycol-β, β-dichlorovinyl phosphate
bis(triethylene glycol-β,β-dichlorovinyl phosphate)
poly(triethylene glycol-β, β-dichlorovinyl phosphate)
tributylene glycol-β,β-dichlorovinyl phosphate
bis(tributylene glycol-β,β-dichlorovinyl phosphate)
tris(tributylene glycol-β, β-dichlorovinyl phosphate)
tris(triethylene glycol-β, β-dichlorovinyl phosphate)
poly(tributylene glycol-β, β-dichlorovinyl phosphate)
dibutylene glycol-β, β-dichlorovinyl phosphate
bis(dibutylene glycol-β,β-dichlorovinyl phosphate)
tris(dibutylene glycol-β,β-dichlorovinyl phosphate)
poly(dibutylene glycol-β,β-dichlorovinyl phosphate)
trihexylene glycol-β,β-dichlorovinyl phosphate
bis(trihexylene glycol-β, β-dichlorovinyl phosphate)
tris(trihexylene glycol-β, β-dichlorovinyl phosphate)
poly(trihexylene glycol-β, β-dichlorovinyl phosphate)
tripropylene glycol-β, β-dibromovinyl phosphate
bis(tripropylene glycol-β, β-dibromovinyl phosphate)
tris(tripropylene glycol-β,β-dibromovinyl phosphate)
poly(tripropylene glycol-β,β-dibromovinyl phosphate)
dipropylene glycol-β, β-dibromovinyl phosphate
poly(dipropylene glycol-β,β-dibromovinyl phosphate)

poly(triethylene glycol-β,β-dibromovinyl phosphate)
poly(dibutylene glycol-β, β-dibromovinyl phosphate)
poly(tributylene glycol-β,β-dibromovinyl phosphate)
poly(trihexylene glycol-β,β-dibromovinyl phosphate)
the monomer, dimer, trimer, and higher polymer of polypropylene glycol-β,β-dichlorovinyl and dibromovinyl phosphates wherein the polypropylene glycol has an average of 14 ether units; the monomer, dimer, trimer and higher polymer of a polyethylene glycol-β,β-dichlorovinyl and dibromovinyl phosphates wherein the polyethylene glycol has an average of 2 ether units,
poly(dipropylene glycol-α-methyl-β,β-dichlorovinyl phosphate),
poly(tripropylene glycol-α-methyl-β,β-dichlorovinyl phosphate),
poly(tributylene glycol-α-methyl-β,β-dichlorovinyl phosphate),
poly(tripropylene glycol-α-trichloromethyl-β,β-dichlorovinyl phosphate), poly(dipropylene glycol-α-methyl-β,β-dibromovinyl phosphate), poly(tripropylene glycol-α-methyl-β,β-dibromovinyl phosphate), mixtures thereof and the like. It is understood that the compounds of the present invention are usually obtained as mixtures of the monomer, dimer, trimer and polymer rather than as the pure compounds. However, these mixtures perform as well in the urethane foams as the unmixed compound.

In accordance with the present invention, a tertiary phosphite is initially reacted with a polyalkylene glycol to yield the intermediate polyalkylene glycol phosphite. The term "tertiary phosphite" as used herein is meant to designate compounds having the formula:

wherein $R_1$, $R_2$ and $R_3$ are each alkyl having from 1 to about 10 carbon atoms or aryl. Illustrative of the alkyl groups are methyl, ethyl, propyl, butyl, hexyl and the like. The term alkyl is also intended to include substituted alkyl groups, including aromatic substituted alkyls such as benzyl and the like. Illustrative of the aryl groups are phenyl and naphthyl groups and substituted forms thereof. The tertiary phosphites which are preferred for use in the present invention are trimethyl phosphite, triethyl phosphite, triisopropyl phosphite, tributyl phosphite, triphenyl phosphite, dimethyl ethyl phosphite, and methyl diethyl phosphite.

The selected tertiary phosphite is tranesterified with a polyalkylene glycol. The term "polyalkylene glycol" as used herein is meant to designate those compounds having a formula corresponding to:

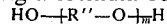

wherein R'' and m are as defined above. Illustrative of the polyalkylene glycols which can be employed in the present invention are: diethylene glycol, triethylene glycol, dipropylene glycol, tripropylene glycol, dibutylene glycol, tributylene glycol, polyethylene glycols where the average number of ether units is 2, polypropylene glycols where the average number of ether units is 14, trihexylene glycol and the like.

The transesterification step is accomplished by reacting the tertiary phosphite with the polyalkylene glycol in approximately a 1:1 molar ratio. By employing this equimolar proportion of reactants, polyalkylene, glycol phosphites having the formula:

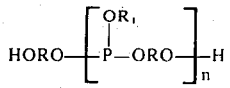

wherein $R_1$, R and n are as defined above, are obtained. The temperature at which the transesterification step is conducted is from about 80°C. to about 200°C. and preferably at from about 100°C. to about 150°C.

This reaction can be improved by employing any of the well known transesterification catalysts. Particularly useful catalysts are the alkali metal alcoholates and phenolates such as sodium methylate, sodium phenolate, sodium decylate and the like. These catalysts are normally employed in an amount from 0.01 to 5 percent, by weight, of the entire reactant mixture. The degree of transesterification can be measured by the quantity of by-product alcohol formed. For example, when 1 mole of trimethyl phosphite is reacted with 1 mole of tripropylene glycol, the transesterification is completed when 2 moles of methanol has been evolved. The reaction time will vary over a wide range depending upon the reactants, temperature and catalyst used. Normally reaction times will be in the range from about 0.5 to 50 hours.

The polyalkylene phosphite produced by the transesterification step is then reacted with a carbonyl compound having the formula:

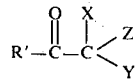

where R', Z and Y are as defined above, with the proviso that the carbonyl compound is one which does not have monohalo- substitution on an alpha carbon atom, and X is bromine or chlorine. Z and Y cannot both by hydrogen or alkyl. These carbonyl compounds can be illustrated by the following: chloral, bromal, 1,1,1-trichloroacetone, 1,1,1-tribromoacetone, hexachloroacetone, dichloroacetaldehyde, dibromoacetaldehyde, dichloromethyl ethyl ketone, trichloromethyl ethyl ketone, and the like. Particularly preferred compounds for use in the present invention are chloral, bromal, dichloroacetaldehyde and dibromoacetaldehyde.

The carbonyl compounds defined above are normally reacted witht he transesterification product in approximately equimolar proportions with respect to the starting tertiary phosphite. The reaction is conducted at a temperature in the range from about 0° to about 100°C., and preferably, at from about 10 to about 40°C. The reaction can be monitored by determining the amount of alkyl or aryl chloride by-product formed. The reaction is complete when approximately 1 mole of chloride has been formed for each mole of carbonyl compound employed.

Both the transesterification and the subsequent reaction with the carbonyl compound can, if desired, be carried out in the presence of a solvent or diluent although this is not necessary to the invention. The solvent or diluent should be non-reactive with respect to both the starting materials and the desired products, and should be miscible therewith. The solvent can also form an azeotrope with the by-product alkanol or phenol of the transesterification step. Illustrative of suitable solvents are benzene xylene, ethylbenzene, diethylbenzene, various alkanes having boiling points greater than that of the by-product, and the like.

The novel compounds of the present invention are characterized by their ability to copolymerize with polyisocyanates employed in forming polyurethanes and by their relatively low acidity. These compounds can completely replace the polyols normally employed in forming the foams or they may be used in combination with the polyols, thereby yielding foams with greatly improved flame resistance. The acid numbers of the compounds of the present invention are normally below about 2 mg. of KOH per gram of the polyalkylene glycol vinyl phosphates. This low acidity makes these compounds relatively unreactive toward the polymerization catalysts employed in producing the polyurethane foams. The high percentage of the flame retardant phosphorus and chlorine atoms present in these compounds reduces the concentration necessary to achieve a flame resistant foam.

A further advantage of the compounds of the present invention is their ability to render the foam self-extinguishing. This characteristic is particularly important in the area of flexible urethane foams. Normally the compounds of the present invention can be employed in amounts of from about 5 to about 30 percent, by weight, of foam to yield self-extinguishing flexible foams. The amount will vary depending upon the particular foam used.

The novel compounds of the present invention can also be used as flame retardants in a wide variety of polymeric systems. Illustrative of these systems are: polyesters, polyolefins, cellulose ethers and esters, urethane coatings and elastomers, polymethyl methacrylates, polyvinyl chlorides and many others. These compounds can be employed in combination with any of the known flame retardants, whether reactive or non-reactive, and can also be used as the sole flame retardant in foams or polymers.

Thus, urethane foams prepared in accordance with the present invention can contain at least one polyalkylene glycol vinyl phosphate in combination with at least one non-reactive, additive type flame retardant which contains atoms or phosphorus, halogen, boron or Group 5A heavy metals. These compounds are well known in the art and are exemplified by the following: the organic esters and amides of phosphoric acid, halogenated, i.e., chlorinated or brominated aliphatic hydrocarbons, including the chlorinated and brominated waxes, oils, and paraffins; halogenated aromatic hydrocarbons such as the chlorinated and brominated di- and triphenyls; metal borates, and in particular the hydrated borates such as zinc borate; and the oxides of antimony, bismuth and arsenic.

The preferred non-reactive, additive type flame retardants for use in the present invention are the organic esters and amides of phosphoric acid, and, in particular, the chlorinated and brominated esters and amides. These compounds are exemplified by the bis and tris (haloalkyl) phosphates, phosphonates and phosphoramidates. Particularly preferred additive flame retardants for the present invention are: tris(2-chloroethyl) phosphate and its thermally condensed polymers, tris(1,3-dichloro-2-propyl)phosphate, tris(2-chloropropyl) phosphate, tris(2,3-dibromopropyl)-phosphate, tris(1-bromo-3-chloro-2-propyl) phosphate, dibromoneopenyl glycol N,N-dimethyl phosphoramidate, dibromomoneopentyl glycol N,N-diethyl phosphoramidate, the halogenated polyphosphonates such as:

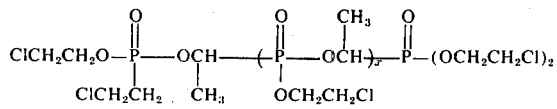

where $x$ is a number from about 0 to about 3, and mixtures thereof. When these particularly preferred additive flame retardants, are blended with the poly(di or tri- propylene or ethylene glycol dichlorovinyl phosphates) and incorporated into the foam forming reaction, there are obtained foams having extremely good flame retardant and physical characteristics, even when compared with the results obtained with other additive flame retardants applicable for use in the process of the present invention. This is particularly true with the combination of poly(dipropylene glycol dichlorovinyl phosphate) and tris(2,3-dibromopropyl) phosphate.

The additive type flame retardants are normally employed in amounts ranging from 1 to about 10 percent by weight of the final foam and preferably from about 2 to 8 percent. The polyalkylene glycol vinyl phosphate and the additive flame retardant will normally be present in a weight ratio of from about 10:1 to about 1:1 with a ratio of from about 5:1 to about 1:1 being preferred.

The urethane foams of the present invention can also contain at least one other reactive flame retardant which contains at least 2% phosphorus, 10% halogen or mixtures thereof and which is distinct from the polyalkylene glycol vinyl phosphates described above. The term "halogen" as used herein is meant to designate chlorine or bromine. These reactive flame retardants, as mentioned above, are those materials containing functional groups which react with the foam forming reagents and are thereby chemically incorporated into the foam. Therefore, polyols containing phosphorus, halogen or mixtures thereof can be employed. Likewise, isocyanates and amines which contain atoms of phosphorus or chlorine are also suitable. Illustrative of these materials are the polyol esters of phosphoric acid; halogenated polyols, in particular, the brominated polyols; halogenated aliphatic and aromatic amines, such as methylene bis(orthochloro)aniline; halogenated aromatic isocyanates, such as chlorinated and brominated toluene diisocyanates; and the like. The preferred compounds for the present invention are of the halogenated polyol type and, in particular, those halogenated polyols which contain phosphorus.

Illustrative of these preferred compounds are the following: bis(polyoxyethylene)hydroxymethyl phosphonate; poly(tripropylene glycol hydrogen phosphonates), dialkyl N,N'-bis(2-hydroxyethyl)aminomethyl phosphonate; dibromoneopentyl glycol; the adipic acid adduct of dibromoneopentyl glycol (having a hydroxyl number approximately equal to 150); the propylene oxide adducts of dibromoneopentyl glycol (having hydroxyl number from about 220 to about 250); 2,3-dibromobutene-1,4-diol; the tetrabromophthalic glycol esters (particularly those derived from the reaction of tetrabromophthalic anhydride with diethylene glycol and propylene oxide); and brominated fatty acid ($C_{10}$–$C_{20}$ compounds sold under the names "Brominex 150P, 160P, or 161P", by Swift and Company, having 2.6% phosphorus and 35% bromine.

The reactive flame retardants are normally employed in amounts ranging from 1 to about 10 percent by weight of the final foam and preferably from about 2 to about 8 percent. The polyalkylene glycol vinyl phosphate and the reactive flame retardant will normally be present in a weight ratio of from about 10:1 to about 1:1 with a ratio of from about 5:1 to about 1:1 being preferred.

The specific proportion of each component of these blends as well as the overall concentration of the blend in the polyurethane foam will, of course, be dependent upon such factors as the degree of flame retardancy desired, the particular end use of the foam, the particular polyalkylene glycol vinyl phosphate and reactive or non-reactive flame retardant used and the foam constituents which are utilized.

The present invention will be further illustrated by the following examples. Unless otherwise stated, all parts and percentages are by weight.

EXAMPLE 1

To a 500 ml. flask fitted with a thermometer, mechanical stirrer and distilling head was charged 402 grams (3 moles) of dipropylene glycol, 372 grams (3 moles) of trimethyl phosphite and 1.5 grams of sodium methylate under a nitrogen atmosphere. The mixture was heated to 110°C. and maintained at this temperature for 8 hours. Then, pressure was reduced by water aspiration to approximately 15 millimeters of Hg and the temperature was kept at 100°C. for another hour. The resulting mixture was cooled in an ice bath and the distilling head was replaced with a dropping funnel containing 442.5 grams (3 moles) of chloral. The chloral was added dropwise while maintaining the temperature below 30°C. by means of an ice bath. The mixture was then allowed to stand at room temperature overnight. The volatiles were removed from the product at 50°C. and 0.3 mm. pressure, leaving 886 grams of a viscous clear oil (98% yield). An infrared analysis revealed vinyl stretching frequency at $1630^{-1}$ cm. Analysis of the product confirmed the structure to be poly(-dipropylene glycol-$\beta$, $\beta$-dichlorovinyl phosphate) having an average n value of 6. In addition, it has an acid number of 0.1 milligram of KOH/gram of product.

EXAMPLE 2

Employing the method of Example 1, 192 grams (1 mole) of tripropylene glycol was reacted with 124 grams (1 mole) of trimethyl phosphite in the presence of 0.5 grams of sodium methylate. After removal of the methanol, 147.4 grams (1 mole) of chloral was added. Again, the temperature was maintained below 30°C. during the addition of the chloral. Isolation of the product yielded 475 grams was 99.5 percent of theoretical. The acid number of the product was 1.4 mg. KOH/g sample. The product was shown by I.R. and Elemental Analysis to be poly (tripropylene glycol-$\beta$,$\beta$-dichlorovinyl phosphate) having an average n value of 5.

EXAMPLE 3

106 grams (1 mole) of diethylene glycol was reacted with 124 grams (1 mole) of trimethyl phosphite in the presence of 0.37 grams of sodium methylate according to the procedure of Example 1. To the resulting reaction product was added 100 ml. of benzene and this mixture was then cooled by means of an ice bath. A mixture of 100 ml. of benzene and 147.4 grams (1 mole) of chloral was then added dropwise to the reaction product mixture while maintaining the temperature below 30°C. This mixture was then stirred overnight at room temperature. The benzene and other volatiles were then removed at 80°C. under reduced pressure. The product was a light yellow viscous oil having an acid number of 1.31. The product was analyzed and shown to be poly(diethylene glycol-$\beta$,$\beta$-dichlorovinyl phosphate) having an average n value of 7.

EXAMPLE 4

268 grams (2 moles) of dipropylene glycol was reacted with 248 grams (2 moles) of trimethyl phosphite in the presence of 0.75 grams of sodium methoxide according to the procedures of Example 1. To the reaction product was added, with stirring, 500 ml. of benzene and this mixture was stirred overnight at room temperature. Next, 323 grams (2 moles) of trichloroacetone was added dropwise to the benzene reaction mixture over a period of 3 hours while maintaining the temperature in the range from about 15° to about 25°C. After the product had been allowed to sit at room temperature overnight, it was heated to 50°C. for 4 hours. An aspirator was used to reduce the pressure and the volatile components were removed at 50°C. yielding a colorless oil in a product yield of 90% of the theoretical yield. The product has an acid number of 1.53 and analysis showed it to be poly(diptopylene glycol-$\alpha$-methyl-$\beta$,$\beta$-dichlorovinyl phosphate) having an average n value of 6.

EXAMPLE 5

33.5 grams (0.25 moles) of dipropylene glycol was reacted with 31.0 grams (0.25 moles) of trimethyl phosphite according to the procedure of Example 1. 100 ml. of benzene was added and the temperature of the reactant mixture was lowered to 10°C. by means of an ice bath. Next, 70.3 grams (0.25 moles) of bromal was added dropwise over a period of 75 minutes, while maintaining the temperature at 10°C. After completion of the addition, the reactant mixture was allowed to come up to room temperature and stirred for several hours. The temperature was then raised to 50°C. for another hour and a half. Stripping off the volatiles at 65°C. followed by aspiration at reduced pressure, then at high vacuum, yielded 93.5 grams of a dark brown viscous oil. Analysis showed this to be poly(dipropylene glycol-$\beta$,$\beta$-dibromovinyl phosphate.

EXAMPLE 6

Employing the procedure of Example 1, 536 grams (4 moles) of dipropylene glycol was reacted with 496 grams (4 moles) of trimethyl phosphite in the presence of 1.5 grams of sodium methoxide, and the resulting reaction product was then reacted with 588 grams (4 moles) of chloral in 500 ml. of benzene. The product was a light yellow oil having an acid number of 0.93 milligrams of KOH/gram of product. This product was then incorporated into a foam formulation as set forth in Table 1.

TABLE I

|  | Grams |
|---|---|
| Polyol, (3000 M.W. triol, propoxylated glycerol) (ethylene oxide-capped) | 100 |
| The compound of Example 6 | 30 |
| Silicone sulfactant | 1.0 |
| Water | 3.9 |
| Dimethyl ethanolamine (DMEA) | 0.30 |
| 1-(N,N-dimethylaminoethyl)-4-methylpiperazine | 0.10 |
| Methylene chloride | 3.0 |
| Stannous octoate, 50% solution in dioctyl phthalate | 0.60 |

Upon addition of 52.9 g. of toluene diisocyanate (80%, 2,4 and 20%, 2,6 isomers), this mixture yielded a flexible urethane foam with good physical and flame retardancy properties. The foam was self-extinguishing and exhibited no differences in physical properties when compared with a similar foam formulated without the compound of Example 6.

EXAMPLE 7

This example illustrates the preparation of a polyurethane foam incorporating two-component flame retardant blends of reactive and non-reactive flame retardants in accordance with this invention. It also provides a comparison with foams which contain each of the individual components of these blends as well as a control formulation which did not contain either of the components.

A number of different urethane foams are prepared by admixing their respective ingredients in the sequence in which they are listed in the following Table 2. The amounts are listed in parts per hundred parts of the base polyol.

In carrying out this procedure, all of the ingredients, with the exception of the TDI are thoroughly admixed with one another, whereupon the TDI is introduced thereby initiating the foam forming reaction. In each case, the TDI index of the resulting foams is 107, the latter factor being computed as follows:

$$\text{TDI INDEX} = \frac{\text{Equivalents of —NCO Groups}}{\text{Total equivalents of —OH Groups in the polyol, the flame retardants and water}} \times 100$$

The following Table 3 presents the flame retardancy and physical property data for each of the foams which are prepared. The physical properties which are evaluated are:
1. Rise Time - The time required for the foam to rise. A rise time of from about 0.5 to 2.0 minutes is acceptable.
2. Density - A density of from about 1.2 – 2.0 pounds per cubic foot is acceptable.
3. Air Flow - This is an evaluation of the porosity of the foam in terms of the air flow, flow rate in cubic feet per minute, required to maintain a constant pressure differential of 0.5 inches of $H_2O$ across the one inch dimension of a 2 inch × 2 inch × 1 inch specimen of the foam which is placed in an apparatus which maintains a vacuum across the rear surface of the specimen. An air flow value greater than 2 cubic feet per minute is considered satisfactory.

TABLE 2

|  | FOAM No. 1 | FOAM No. 2 | FOAM No. 3 | FOAM No. 4 | FOAM No. 5 | FOAM No. 6 | FOAM No. 7 | FOAM No. 8 | FOAM No. 9 | FOAM No. 10 | FOAM No. 11 |
|---|---|---|---|---|---|---|---|---|---|---|---|
| The poly(dipropylene glycol vinyl phosphate) as prepared according to Example 1 | — | 0 | 25 | 25 | 15 | 15 | 15 | 15 | 15 | 15 | 15 |
| Tris(2,3-dibromopropyl)phosphate | — | 5 | — | — | 5 | 5 | — | — | — | — | — |
| Tris(2-chloroethyl)phosphate | — | — | — | — | — | — | — | — | — | 5 | — |
| Tris(1,3-dichloro-2-propyl)phosphate | — | — | — | — | — | — | — | — | — | — | 5 |
| Mixture of Chlorinated polyphosphonates[1] | — | — | — | — | — | — | — | 5 | — | — | — |
| Dibromoneopentylglycol N,N-dimethyl phosphonamidate | — | — | — | — | — | — | 5 | — | — | — | — |
| A polyol comprising a propylene oxide adduct of glycerine having some ethylene oxide capping and a molecular weight of about 3,000 sold by the Jefferson Chemical Company as "THANOL F-3002" | 100 | — | 100 | 100 | 100 | 100 | 100 | 100 | — | — | — |
| Polyol-propylene oxide adduct of glycerine having a molecular weight of 3,000 and sold by Olin Mathieson as Poly C-3030 | — | 100 | — | — | — | — | — | — | 100 | 100 | 100 |
| A silicone surfactant sold by the Union Carbide Corp. as "L-540" | 1.0 | 0.9 | 1.0 | 1.0 | 1.0 | 1.0 | 1.0 | 1.0 | 0.9 | 0.9 | 0.9 |
| Water | 3.9 | 4.0 | 3.9 | 4.5 | 3.9 | 4.5 | 3.9 | 3.9 | 4.0 | 4.0 | 4.0 |
| 2-(dimethylamino)ethyl ether (Catalyst) | 0.14 | 0.17 | 0.14 | 0.14 | 0.14 | 0.14 | 0.14 | 0.14 | 0.17 | 0.17 | 0.17 |
| N-ethyl morpholine (Catalyst) | 0.20 | 0.20 | 0.20 | 0.20 | 0.20 | 0.20 | 0.20 | 0.20 | 0.20 | 0.20 | 0.20 |
| 1,4-diazobicyclic [2,2,2] octane (Catalyst) 33% solution in dipropylene glycol | 0.30 | — | 0.30 | 0.30 | 0.30 | 0.30 | 0.30 | 0.30 | — | — | — |
| Methylene Chloride (Blowing Agent) | 3 | 3 | 3 | 3 | 3 | 3 | 3 | 3 | 3 | 3 | 3 |
| A 50% solution of stabilized stannous octoate in dioctyl phthalate (Catalyst) | 0.30 | 0.40 | 0.30 | 0.30 | 0.30 | 0.30 | 0.30 | 0.30 | 0.40 | 0.40 | 0.40 |
| An 80:20 mixture of 2,4-and 2,6-toluene diisocyanate (TDI) | 50.1 | 51.1 | 52.2 | 58.5 | 51.3 | 57.55 | 51.7 | 52 | 52 | 52 | 52 |

[1]A mixture of chlorinated polyphosphanates having the formula:

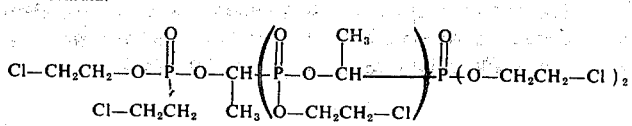

where x is an integer having a value of from about 0 to 3.

4. 50% and 90% Compression Set - In these tests, a 2 inch × 2 inch × 1 inch specimen of the foam is compressed in the 1 inch dimension, down to a thickness of 0.5 inch and 0.1 inch respectively, and held in these positions for 22 hours at 70°C. Upon releasing the pressure, the amount of set, i.e., the extent to which the foam has been compressed, is measured. Thus, if the foam returns to its original 1 inch width, it has a zero set. Accordingly, low values, no higher than about 20%, are desirable in this test as being indicative of a high degree of resistance to permanent deformation.

5. The Autoclave Compression Set - This test is conducted in the same manner as the above after the foams have been placed in a steam autoclave at 200°F. for 3 hours prior to testing. Acceptable reading are below about 30.

6. The Compression Load Deflection - Measures the firmness of the foam. It is the force in pounds per square inch need to deflect the foams to 25 and 65 percent of its thickness.

The flame retardancy characteristics of the various foams are determined by means of the following procedure.

1. ASTM Test D-1692 - This test evaluates the surface flammability of the foams by supporting a 6 inch × 2 inch × 0.5 inch foam specimen on a horizontal hardware-cloth with the 0.5 inch dimension vertical and contacting one end for 60 seconds with a 1.5 inch high blue flame from a ⅜ inch diameter barrel bunsen burner fitted with a 1⅞ inch side wing top. During the course of this test, it is determined whether the sample is selfextinguishing or whether it continues to burn until it is completely extinguished.

2. Dry Heat Aging Test - This test is identical to ASTM test D-1692 with the exception that the foam samples are first dry heat aged at 140°C. for 22 hours prior to being burned. Thus, it is a far more rigorous test since the foam is in a drier, more flammable condition before being burned and many foams lose their additive flame retardants by volatilization.

3. Limiting Oxygen Index (LOI) - This test is conducted by means of the procedure described by Fenimore and Martin in the November, 1966, issue of Modern Plastics. In brief, this procedure directly relates flame retardancy to a measurement of the minimum percentage concentration of oxygen in an oxygen:nitrogen mixture which permits the sample to burn; the LOI being calculated as follows:

$$LOI = \frac{[O_2]}{[O_2] + [N_2]} \times 100$$

Thus, a higher LOI is indicative of a higher degree of flame retardancy.

The following Table 3 presents the results of this evaluation.

TABLE 3

|  | FOAM No.1 | FOAM No.2 | FOAM No.3 | FOAM No.4 | FOAM No.5 | FOAM No.6 | FOAM No.7 | FOAM No.8 | FOAM No.9 | FOAM No.10 | FOAM No.11 |
|---|---|---|---|---|---|---|---|---|---|---|---|
| Rise Time (Seconds) | 78 | 109 | 80 | 80 | 80 | 80 | 116 | 113 | 146 | 165 | 140 |
| Density (lbs/cu.ft) | 1.37 | 1.58 | 1.62 | 1.49 | 1.57 | 1.46 | 1.60 | 1.81 | 1.74 | 1.88 | 1.67 |
| Airflow (Cu.ft/min) | 5.4 | 5.6 | 2.6 | 2.4 | 3.1 | 3.9 | 5.8 | 4.0 | 3.7 | 4.5 | 6.0 |
| 90% Compression Set (Percent Set) | 8 | 15 | 36 | 32 | 14 | 10 | 8 | 12 | 9 | 8 | 9 |
| 50% Compression Set (Percent Set) | — | — | 9 | 8 | 7 | 6 | — | — | — | | |
| Autoclave Compression Set (Percent Set) | — | 20 | 90 | 90 | 31 | 16 | 14 | 19 | 11 | 8 | 8 |
| Flammability rating (ASTM Test 1692)[1] [2] | B | SE | SE | SE | SE | SE | B | SE | SE | SE | SE |
| Dry Heat Aged Flammability (ASTM D1692) | B | B | SE | SE | SE | SE | SE | SE | SE | SE | SE |
| Compression Load Deflection (lb/sq.in)(CLD)25% | — | — | 0.25 | 0.34 | 0.34 | 0.36 | — | — | — | — | — |
| (lb/sq.in)(CLD)65% | — | — | 0.39 | 0.51 | 0.54 | 0.52 | — | — | — | — | — |
| Autoclave CLD 25% (lb/sq.in.) | — | — | 0.21 | 0.31 | 0.29 | 0.33 | — | — | — | — | — |
| Autoclave CLD 65% (lb/sq.in.) | — | — | 0.38 | 0.51 | 0.57 | 0.52 | — | — | — | — | — |
| LOI | — | — | 22.3 | 22.8 | 22.6 | 22.3 | — | — | — | — | — |

[1] SE = Self-Extinguishing
[2] B = Burns

The results contained in Table 3 demonstrate the benefits of blends obtained in accordance with the present invention. Foam No. 1 (the control) does not contain any flame retardants and burns under flame test conditions. Foam No. 2 contains only the non-reactive flame retardant and, though being self extinguishing initially, burns after dry heat aging. Foams No. 3 and No. 4 contain only the polyalkylene glycol vinyl phosphate. Foams No. 5 and No. 6 contain the blend of the present invention but at lower concentrations of flame retardant than contained in Foam No. 3 and No. 4. Foams No. 5 and No. 6 exhibit similar flame retardance while having physical properties superior to Foams No. 3 and No. 4 respectively. Foam No. 7 contains only the polyalkylene glycol vinyl phosphate, but at lower concentration that Foams No. 3 and No. 4. Foam No. 7 burns prior to dry heat aging.

Foams No. 8, 9, 10 and 11 demonstrate the good flame retardancy and physical characteristics obtained when the blends of the present invention are employed. Similarly, excellent results are obtained when tris(2-chloropropyl) phosphate and tris(1-bromo-3-chloro-2-propyl)phosphate are substituted for the tris(2,3-dibromopropyl)phosphate of Foams No. 5 and 6. Likewise, good results are obtained when polyalkylene glycol vinyl phosphates of Examples 2, 3 and 4 are substituted for the poly(dipropylene glycol-β,β-dichlorovinyl phosphate) of Example 1 in Foams No. 5 and 6.

EXAMPLE 8

A foam is blended according to the procedure of Example 7, Foam No. 7 with the exception that 3 parts per hundred of antimony oxide are added prior to addition of the isocyanate. The resultant foam has excellent flame retardance, both initially and after dry heat aging, while exhibiting good physical properties.

EXAMPLE 9

This example illustrates the preparation of a polyurethane foam incorporating two-component flame retardant blends of polyalkylene glycol vinyl phosphates and other reactive flame retardants in accordance with this invention. It also provides a comparison with foams which contain each of the individual components of these blends as well as a control formulation which did not contain either of the components.

A number of different urethane foams are prepared by admixing their respective ingredients in the sequence in which they are listed in the following Table 4. The amounts are listed in parts per hundred parts of the base polyol.

TABLE 4

| | FOAM No.1 | FOAM No.2 | FOAM No.3 | FOAM No.4 | FOAM No.5 | FOAM No.6 | FOAM No.7 | FOAM No.8 | FOAM No.9 | FOAM No.10 | FOAM No.11 | FOAM No.12 | FOAM No.13 | FOAM* No.14 |
|---|---|---|---|---|---|---|---|---|---|---|---|---|---|---|
| The poly(dipropylene glycol vinyl phosphate) as prepared according to Example 1 | — | 15 | 15 | 15 | 15 | 15 | 15 | 15 | 15 | 15 | 15 | 15 | 15 | 15 |
| dibromoneopentyl glycol | — | — | 5 | 5 | — | — | — | — | — | — | — | — | — | — |
| adipic acid adduct of dibromoneopentyl glycol (OH No.=150) | — | — | — | — | 5 | — | — | — | — | — | — | — | — | — |
| propylene oxide adduct of dibromoneopentyl glycol (OH No.=220) | — | — | — | — | — | 5 | — | — | — | — | — | — | — | — |
| propylene oxide adduct of dibromoneopentyl glycol (OH No.=250) | — | — | — | — | — | — | 5 | — | — | — | — | — | — | — |
| Brominex 150 P | — | — | — | — | — | — | — | 5 | 5 | — | — | — | — | — |
| Brominex 160 P | — | — | — | — | — | — | — | — | — | 5 | — | — | — | — |
| Brominex 161 P | — | — | — | — | — | — | — | — | — | — | 5 | — | — | — |
| Esterification product of tetrabromophthalic anhydride, propylene oxide and diethylene glycol | — | — | — | — | — | — | — | — | — | — | — | 5 | — | — |
| 2,3-dibromobutene-1,4 diol | — | — | — | — | — | — | — | — | — | — | — | — | — | 5 |
| 2,3-dibromopropanol | — | — | — | — | — | — | — | — | — | — | — | — | 5 | — |
| A polyol comprising a propylene oxide adduct of glycerine having some ethylene oxide capping and a molecular weight of about 3,000 sold by the Jefferson Chemical Company as "THANOL F-3002" | 100 | 100 | 100 | — | 100 | 100 | 100 | — | — | — | — | — | — | — |

TABLE 4-continued

| | FOAM No.1 | FOAM No.2 | FOAM No.3 | FOAM No.4 | FOAM No.5 | FOAM No.6 | FOAM No.7 | FOAM No.8 | FOAM No.9 | FOAM No.10 | FOAM No.11 | FOAM No.12 | FOAM No.13 | FOAM* No.14 |
|---|---|---|---|---|---|---|---|---|---|---|---|---|---|---|
| A polyol comprising a propylene oxide adduct of glycerol having a molecular weight of about 3000 sold by Union Carbide as "NIAX LG-56" | — | — | — | 100 | — | — | — | — | 100 | 100 | 100 | 100 | 100 | — |
| A silicone surfactant sold by the Union Carbide Corp. as "L-540" | 1.0 | 1.0 | 1.0 | 0.9 | 1.0 | 1.0 | 1.0 | 1.0 | 0.9 | 0.9 | 0.9 | 0.9 | 0.9 | 0.9 |
| Water | 3.9 | 3.9 | 3.9 | 4.0 | 3.9 | 3.9 | 3.9 | 3.9 | 3.9 | 4.0 | 4.0 | 4.0 | 4.0 | 4.0 |
| 2-(dimethylaminoethyl) ether (Catalyst) | 0.14 | 0.14 | 0.14 | 0.17 | 0.14 | 0.14 | 0.14 | 0.14 | 0.17 | 0.17 | 0.17 | 0.17 | 0.17 | 0.17 |
| N-ethyl morpholine (Catalyst) | 0.2 | 0.2 | 0.2 | 0.2 | 0.2 | 0.2 | 0.2 | 0.2 | 0.2 | 0.2 | 0.2 | 0.2 | 0.2 | 0.2 |
| 1,4-diazobicyclo [2.2.2] octane (Catalyst) | 0.3 | 0.3 | 0.3 | — | 0.3 | 0.3 | 0.3 | 0.3 | — | — | — | — | — | — |
| 33% Solution Methylene Chloride (Blowing Agent) | 3.0 | 3.0 | 3.0 | 3.0 | 3.0 | 3.0 | 3.0 | 3.0 | 3.0 | 3.0 | 3.0 | 3.0 | 3.0 | 3.0 |
| A 50% solution of stabilized stannous octoate in dioctyl phthalate (Catalyst) | 0.45 | 0.45 | 0.30 | 0.40 | 0.35 | 0.45 | 0.45 | 0.45 | 0.40 | 0.40 | 0.40 | 0.40 | 0.40 | 0.40 |
| An 80:20 mixture of 2,4-and 2,6-toluene diisocyanate (TDI) | 50.1 | 51.7 | 55.2 | 56.3 | 52.9 | 53.7 | 53.8 | 52.0 | 53.1 | 53.1 | 53.2 | 54.1 | 55.8 | 55.5 |

*Foam No. 14 contained a propylene oxide adduct of glycerine having a moleculaar weight of 3000 and sold by Olin Mathieson as "POLYOL 3030"

In carrying out this procedure, all of the ingredients, with the exception of the TDI are thoroughly admixed with one another, whereupon the TDI is introduced thereby initiating the foam forming reaction. In each case, the TDI index as defined in Example 7 of the resulting foams is 107.

The following Table 5 presents the flame retardancy and physical property data for each of the foams which are prepared. The physical properties which are evaluated are defined in Example 7.

TABLE 5

| | FOAM No.1 | FOAM No.2 | FOAM No.3 | FOAM No.4 | FOAM No.5 | FOAM No.6 | FOAM No.7 | FOAM No.8 | FOAM No.9 | FOAM No.10 | FOAM No.11 | FOAM No.12 | FOAM No.13 | FOAM No.14 |
|---|---|---|---|---|---|---|---|---|---|---|---|---|---|---|
| Rise Time (Seconds) | 78 | 116 | 116 | 129 | 127 | 104 | 107 | 110 | 153 | 132 | 146 | 141 | 144 | 152 |
| Density (lbs/cu.ft.) | 1.37 | 1.60 | 1.66 | 1.66 | 1.73 | 1.62 | 1.80 | 1.72 | 1.69 | 1.65 | 1.71 | 1.71 | 1.72 | 1.69 |
| Air flow (cu.ft./min.) | 5.4 | 5.8 | 5.0 | 2.7 | 1.3 | 2.0 | 2.0 | 2.0 | 5.0 | 5.5 | 5.7 | 4.5 | 3.2 | 1.4 |
| 90% Compression Set -(4 day) | 8 | 8 | 26 | 22 | 13 | 22 | 19 | 25 | 10 | 10 | 10 | 10 | 23 | 21 |
| Autoclave 90% Compression Set - | 24 | 14 | 40 | 32 | 26 | 45 | 53 | 51 | 9 | 9 | 12 | 25 | 49 | 45 |
| Flammability (ASTM Test 1692[(1)]) | B | B | S.E. | — | S.E. | S.E. | S.E. | S.E. | — | — | — | — | — | S.E. |
| Dry Heat Aged Flammability[(1)] | B | S.E. | S.E. | S.E. | S.E. | S.E. | S.E. | S.E. | S.E. | S.E | S.E | S.E. | S.E. | — |

B = burn
S.E. = self-extinguishing

The results contained in Table 5 demonstrate the excellant flame retardancy, both initially and upon dry heat aging, of the foams employing blends in accordance with the present invention. Furthermore, these hand blended foams exhibit relatively little loss in physical properties, normally being within the typical tolerance listed above. It is obvious that further improvement in physical properties can be obtained by machine blending, as is well known in the art, thereby rendering foams within the desired tolerances.

EXAMPLE 10

Three foams are blended in like manner to Foam No. 3 of Table 4 in Example 9 except that dibromoneopentyl glycol is replaced by 5 parts of poly(tripropylene glycol hydrogen phosphonate); diethyl-N,N-bis(2-hydroxyethyl)aminomethyl phosphonate; and bis(-polyoxyethylene)hydroxymethyl phosphonate, respectively. Each yields a self-extinguishing foam having good physical properties.

Excellent results are also obtained when the polyalkylene glycol vinyl phosphates of Examples 2, 3 and 4 are substituted for the poly(dipropylene glycol-β,β-dichlorovinyl phosphate) of Example 1 in Foams Nos. 3 to 14.

What is claimed is:

1. Polyalkylene glycol vinyl phosphates having the formula:

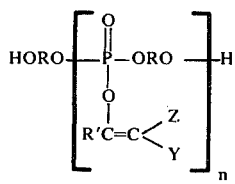

wherein R is a polyalkylene glycol residue defined as that portion remaining after two hydroxyl groups have been removed from a polyalkylene glycol having the formula:

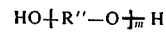

where R'' is an alkylene group of from 2 to about 20 carbon atoms, and m designates the number of repeating alkylene ether units and is from 2 to about 20, $n$ is an integer from 1 to about 100, R' is selected from the group consisting of hydrogen, alkyl and haloalkyl having from 1 to 4 carbon atoms, Z and Y are each selected from the group consisting of halogen, hydrogen and alkyl, provided Z and Y are not both hydrogen ar alkyl.

2. A composition according to claim 1 wherein R is a tripropylene glycol residue.

3. A composition according to claim 1 wherein R is a triethylene glycol residue.

4. A composition according to claim 1 wherein Y and Z are selected from the group consisting of chlorine and bromine.

5. A composition according to claim 4 wherein R' is hydrogen.

6. A composition according to claim 5 wherein R is a tripropylene glycol residue.

7. A composition according to claim 5 wherein R is a dipropylene glycol residue.

8. A composition according to claim 5 wherein R is a diethylene glycol residue.

* * * * *